(12) United States Patent
Klever et al.

(10) Patent No.: US 10,207,063 B2
(45) Date of Patent: Feb. 19, 2019

(54) NEBULIZER AND SPACER FOR THE TOPICAL APPLICATION OF A LIQUID AND/OR SOLID TO A SURFACE

(71) Applicant: Dutch Renewable Energy B.V., Muiden (NL)

(72) Inventors: Diede Hendrik Paul Klever, Amsterdam (NL); Hubert Clemens Pellikaan, Utrecht (NL); Rolf Lourens Visser, Breukelen (NL)

(73) Assignee: Dutch Renewable Energy B.V., Muiden (NL)

( * ) Notice: Subject to any disclaimer, the term of this patent is extended or adjusted under 35 U.S.C. 154(b) by 213 days.

(21) Appl. No.: 15/325,966

(22) PCT Filed: Jul. 15, 2015

(86) PCT No.: PCT/NL2015/050517
§ 371 (c)(1),
(2) Date: Jan. 12, 2017

(87) PCT Pub. No.: WO2016/010428
PCT Pub. Date: Jan. 21, 2016

(65) Prior Publication Data
US 2017/0189627 A1    Jul. 6, 2017

(30) Foreign Application Priority Data
Jul. 15, 2014   (NL) .................................... 2013186

(51) Int. Cl.
*A61M 11/02* (2006.01)
*B05B 1/28* (2006.01)
(Continued)

(52) U.S. Cl.
CPC ............ *A61M 11/02* (2013.01); *A61M 35/00* (2013.01); *B05B 1/169* (2013.01); *B05B 1/1663* (2013.01);
(Continued)

(58) Field of Classification Search
CPC .... A61M 11/02; A61M 11/04; A61M 11/045; A61M 11/006; A61M 11/007;
(Continued)

(56) References Cited

U.S. PATENT DOCUMENTS

| | | | | |
|---|---|---|---|---|
| 3,447,722 A | * | 6/1969 | Mason | B65D 83/14 137/607 |
| 4,417,674 A | * | 11/1983 | Giuffredi | B65D 83/48 222/402.18 |

(Continued)

FOREIGN PATENT DOCUMENTS

| | | |
|---|---|---|
| GB | 1263521 A | 2/1972 |
| GB | 2018908 A | 10/1979 |

(Continued)

*Primary Examiner* — Philip R Wiest
(74) *Attorney, Agent, or Firm* — Bret E. Field; Bozicevic, Field & Francis LLP (57) ABSTRACT

The present invention relates to a nebulizer, such as a spray can, for the topical application of a liquid and/or solid to a surface. The nebulizer is characterized by a valve comprising a mixing chamber designed for forming a colloidal mixture comprising a dispersed phase consisting of a liquid and/or a solid substance and a continuous phase consisting of a propellant gas before delivering the colloidal mixture to the nozzle. The invention also relates to a method for the topical cooling of the skin of a person or animal. In addition, the invention relates to various other uses of the device.

16 Claims, 7 Drawing Sheets

(51) Int. Cl.
  *B65D 83/44* (2006.01)
  *B05B 1/16* (2006.01)
  *B05B 7/24* (2006.01)
  *B65D 83/30* (2006.01)
  *B65D 83/36* (2006.01)
  *B65D 83/14* (2006.01)
  *B65D 83/56* (2006.01)
  *A61M 35/00* (2006.01)
  *B65D 83/48* (2006.01)
  *B05B 7/04* (2006.01)

(52) U.S. Cl.
  CPC .............. *B05B 1/28* (2013.01); *B05B 7/0483* (2013.01); *B05B 7/2432* (2013.01); *B65D 83/306* (2013.01); *B65D 83/36* (2013.01); *B65D 83/44* (2013.01); *B65D 83/48* (2013.01); *B65D 83/565* (2015.07); *B65D 83/7532* (2013.01); *B05B 7/0416* (2013.01)

(58) Field of Classification Search
  CPC ... A61M 35/00; B65D 83/565; B65D 83/306; B65D 83/36; B65D 83/44; B65D 83/48; B65D 83/7532; B05B 1/1663; B05B 1/169; B05B 1/28; B05B 7/0483; B05B 7/2432; B05B 7/0416
  See application file for complete search history.

(56) References Cited

U.S. PATENT DOCUMENTS 5,125,546 A * 6/1992 Dunne ................. B01F 5/0416
                                                222/394
6,883,688 B1    4/2005 Stern et al.

FOREIGN PATENT DOCUMENTS

| | | |
|---|---|---|
| GB | 2410707 A | 8/2005 |
| GB | 2458128 A | 9/2009 |
| JP | H07275759 A | 10/1995 |
| JP | H0824729 A | 1/1996 |
| JP | H08299866 A | 11/1996 |
| WO | WO90/05580 A1 | 5/1990 |

* cited by examiner

NEBULIZER AND SPACER FOR THE TOPICAL APPLICATION OF A LIQUID AND/OR SOLID TO A SURFACE

The invention relates to a nebulizer for the topical application of a liquid and/or solid to a surface. The invention also relates to a method for the topical cooling of the skin of a person or animal and to a cooling medium and various applications of the device according to the present invention.

The invention relates to the topical application of a liquid and/or solid to a surface. Various nebulizers, such as spray cans, are already known for many diverse applications. Such nebulizers comprise a container in which liquid is kept under pressure with a propellant gas or compressed air in order to expel the liquid as a fine-particle spray. To expel the liquid as a fine-particle spray, the known nebulizer has a spray nozzle with a specific bore. The size of the bore created in the nozzle is generally of determining significance for the dispersion of the spray as well as the liquid concentration (for example the number of milligrams per second) in the spray generated by the nozzle.

An example of such a nebulizer is disclosed in United Kingdom patent application GB 2 018 908 A describing a valve for a pressurized dispensing container, wherein the valve comprises a hollow body associated with a drawing tube for the fluid transport and provided with at least one through hole for the gas transport, as well as a shutter element movable in the body against a spring and provided with a hollow stem having at least one opening which can be shut off by a sealing gasket. The body has therein a nozzle which is hydraulically connected with the drawing tube and cooperates with a venturi effect conduit which with such a nozzle defines an annular space communicating with said through hole for the gas transport.

By decreasing the bore size of the nozzle it is possible to create a nebulizer that is designed for generating a spray comprising a low liquid concentration and/or that is designed for the topical, i.e., highly local application of a liquid and/or solid substance.

The present invention provides an improved nebulizer, such as a spray can, for the topical application of a liquid and/or solid to a surface, comprising a container designed for holding a colloidal substance and a medium, an actuatable valve attached to the container and a nozzle attached to the valve, designed for generating a stream or spray. The valve comprises a mixing chamber attached to the nozzle and a first and a second inlet attached to the mixing chamber for the separate delivery of the colloidal substance and the medium to the mixing chamber. The mixing chamber of the nebulizer according to the present invention is designed for forming a colloidal mixture comprising the colloidal substance and the medium before delivering the colloidal mixture to the nozzle, wherein the colloidal mixture comprises a dispersed phase consisting of a liquid and/or a solid substance and a continuous phase consisting of a propellant gas.

The nebulizer of the present invention has the advantage that, due to the formation of a colloidal mixture before delivering the colloidal mixture to the nozzle, the size of the bore of the nozzle does not necessarily have to be adjusted in order to generate a spray with a reduced concentration of liquid and/or solid material and/or to generate a spray that can be applied topically, i.e., very locally, to a surface. The present invention therefore provides a nebulizer that is designed for the highly directed treatment of surfaces.

In an embodiment according to the present invention the contents of the container and, optionally, the actuatable valve attached to the container are held under a pressure greater than atmospheric pressure. Preferably, in the closed state the pressures in the container and in the actuatable valve attached to the container are the same. It is to be noted that if the valve is in the opened state, the pressure in the valve will be lower than the pressure in the container. More preferably the pressure referred to above is greater than 2.0 bar, preferably greater than 3.0 bar, preferably approximately 4.0 bar, preferably approximately 5.0 bar, preferably approximately 12 bar, preferably approximately 60 bar.

The colloidal mixture such as that formed in the mixing chamber preferably comprises a dispersed phase of liquid and a continuous phase of propellant gas. It has been found that a fine spray can be produced which has the properties of a directed liquid stream. The colloidal mixture such as that formed in the mixing chamber can be of various types, but preferably comprises an aerosol.

In order to guarantee the delivery of a colloidal mixture comprising a dispersed phase consisting of a liquid and/or a solid substance and a continuous phase consisting of a propellant gas, the first and/or second inlet attached to the mixing chamber is preferably provided with inlet blocking means, such as a shut-off valve that is opened when the device is brought into the proper orientation for use. Proper orientation is defined here as the position in which the first and second inlets are positioned such that they supply the colloidal substance and the medium via the inlets intended for them in order to form the desired colloidal mixture. Such a blocking means preferably comprises a ball, movable under the influence of gravity, which closes the first and/or second inlet when the nebulizer is in an inactive orientation. Such an inactive orientation comprises for example the orientation of the nebulizer wherein the nozzle is directed in the opposite direction to the direction of the force of gravity. As soon as the nebulizer is rotated into an active orientation (wherein the nozzle is facing in a direction substantially identical to the direction of the force of gravity), the first and/or second inlet that is closed in the inactive orientation is opened and makes the use of the nebulizer possible.

A possible alternative embodiment in order to guarantee the delivery of a colloidal mixture comprising a dispersed phase consisting of a liquid and/or a solid substance and a continuous phase consisting of a propellant gas relates to a nebulizer wherein the colloidal substance and/or the medium is enclosed by a chamber which is only connected to the first and/or second inlet. Such an embodiment also has a nebulizer comprising at least a first and a second partial container, which first partial container is designed for holding a colloidal substance and is connected to the first inlet and wherein the second partial container is designed for holding a medium and is connected to the second inlet. In such a variant embodiment the use of an inlet blocking means is no longer necessary. In such a case the intended colloidal mixture, i.e., a colloidal mixture comprising a dispersed phase consisting of a liquid and/or a solid substance and a continuous phase consisting of a propellant gas, can be formed regardless of the orientation of the nebulizer.

In an embodiment according to the present invention the container of the nebulizer comprises a first vessel for holding the colloidal substance and a second vessel for holding the medium, wherein the pressures in the first vessel and the second vessel are the same. The nebulizer according to the present invention thus provides the possibility of supplying separate vessels which may optionally be combined into one container.

In a further variant embodiment the stream generated by the nozzle comprises a liquid and/or solid matter concentration of a maximum of 100 mg per second. It has been found that the nebulizer provides the possibility of generating a stream comprising a very low concentration of colloidal substance without the bore size of the nozzle having to be adjusted such that clogging of the nozzle threatens to occur. Preferably the liquid and/or solid matter concentration of the stream generated by the nozzle is between 0 and 100 mg per second, more preferably between 20 and 80 mg per second, and even more preferably between 40 and 60 mg per second.

The stream generated by the nozzle of the nebulizer can have the shape of a cone with a top angle of the cone that is smaller than 30°, preferably smaller than 20° and preferably smaller than 10°, preferably smaller than 5°. The nebulizer according to the present invention thus provides a stream that can be directed against a surface to be treated. The top angle of the cone may also optionally be greater than 30°.

The formation of a colloidal mixture in the mixing chamber can be accomplished in various ways. For example it is possible for the mixing chamber to be provided with a Venturi for drawing up the colloidal substance or the medium. Preferably the Venturi comprises a controllable Venturi in order to further regulate the quantity to be applied to a surface. Another possibility for forming a colloidal mixture in the mixing chamber can for example be obtained by providing the first and/or second inlet with an opening for delivering the colloidal substance and/or the medium. Once again this preferably relates to a controllable opening.

In yet another possibility the first and/or second is provided with a resistance, such as a membrane, for delivering the colloidal substance and/or the medium. Here also the resistance may comprise a controllable resistance. In another possible alternative embodiment the first and/or second inlet is provided with a release valve for delivering the colloidal substance and/or the medium. Preferably the release valve comprises a controllable release valve.

To further prevent unintentional discharge of the nebulizer, in one embodiment the nebulizer of the present invention comprises a blocking element. Such a blocking element is designed for blocking the valve in at least one position. A blocking element can for example consist of a lever or slide mechanism, in which the lever or the slide mechanism is placed in a blocking position in the space formed between the bottom edge of the nozzle and the top edge of the container. In this way the lever or the slide mechanism prevents the nozzle from being pressed in to open the valve and activate the nebulizer. The nebulizer can be unlocked by removing the lever or the slide mechanism from the space formed between the bottom edge of the nozzle and the top edge of the container. In the unlocked position the nozzle can be pressed in to open the valve and activate the nebulizer.

It has been found that the nebulizer according to the present invention is extremely well suited for the topical application of a cooling medium. For this purpose the container of the nebulizer is filled with a liquid which cools the skin by evaporation when applied to the skin. In the case of various skin problems, the local withdrawal of heat from the skin can have a remediating or at least an alleviating effect. Examples of skin problems wherein the local cooling of the skin has a remediating or at least an alleviating effect comprise for example (topical) burns, pustules (for example caused by acne), itching (for example nettle rash) and skin irritation due to an insect bite. If very low temperatures can be achieved during the topical application of a cooling medium to the skin, it is also possible to treat skin conditions such as warts. The treatment of skin conditions such as warts preferably takes place at temperatures below the freezing point.

The above-described treatment of skin conditions by the application of a cooling medium to the skin of a person or animal is better known as cryotherapy. In cryotherapy use is frequently made of liquid nitrogen (boiling point: −196° C.) applied with a cotton swab or a nozzle specially designed for the application of nitrogen. Under the marked change in temperature and/or ambient pressure the nitrogen evaporates on contact with the skin, with the result that the skin cools markedly. In addition to liquid nitrogen, use can also be made of a cooling medium with a considerably higher boiling point, such as dimethyl ether, propane and mixtures thereof (boiling point: −57° C.). Mixtures with such boiling points are commercially available.

The ability to apply a cooling medium in a directed manner prevents the surrounding skin, which does not need to be treated, from coming into contact with the cooling medium. Especially when temperatures below the freezing point are used, it is desirable to prevent contact of the surrounding skin with the cooling medium in order to increase the user's comfort. Since freezing of the cooling medium starts as soon as it leaves the nozzle, if the bore of the nozzle is too small, the nozzle will become blocked by frozen cooling medium. By creating a nebulizer in which the valve comprises a mixing chamber that is designed for the immediate formation of a colloidal mixture, cooling medium can be applied to the skin to be treated in a directed manner without requiring a nozzle bore size that can result in clogging of the nozzle.

The valve of the nebulizer according to the present invention is preferably designed for the uninterrupted, i.e., continuous, application of cooling medium. Through the uninterrupted, continuous, delivery of the cooling medium a lower temperature can be achieved than is usual at this time. With a metered dose, i.e., a predetermined quantity, limited cooling of the skin is accomplished. This limited cooling generally achieves a temperature of down to −20° C. Through the uninterrupted delivery of the cooling medium a temperature of below −20° C. can be achieved. Preferably the temperature achieved is below −30° C. Through the uninterrupted delivery of cooling medium a temperature can be achieved which corresponds to the boiling point of the propellant gas, but it is also possible to reach temperatures that are below the boiling point of the propellant gas, for example by further expansion of the propellant gas. For example a temperature of approximately −50° C. can be achieved with 1,1,1,2-tetrafluoroethane (R134a, boiling point: −26.3° C.) as propellant gas.

In one variant embodiment the cooling medium comprises at least one active compound comprising an antiviral agent, terpene and/or essential oil. The advantage of a cooling medium comprising at least one active compound is that in addition to cooling the skin of the user, the skin is also treated with an active compound that has an additional remediating effect.

Preferably the terpene and the essential oil are chosen from camphor, menthol, thymol, thyme oil, eucalyptus, eucalyptus citriodora, turpentine, pine oil, Melaleuca alternifolia, menthone, menthyl salicylate, musk oil, bixa orellana, borneol, curcuma oil, peppermint oil, clove oil, fennel oil, basil oil, patchouli oil, alpha-pinene, terpineol, oregano oil, carvacrol and combinations thereof.

The antiviral agents preferably comprise replication inhibitors, such as cidofovir, acyclovir, pencyclovir and the like. However, other antiviral agents may also be considered.

The cooling medium of the device of the present invention preferably contains a propellant gas which comprises a mixture of hydrocarbons. In one embodiment the propellant gas comprises a cooling agent, in particular a cooling agent with a boiling point below −10° C. Examples of suitable cooling agents of this type comprise propane, n-butane, 1,1,1,2-tetrafluoroethane, dimethyl ether, dimethyl ether/propane mixtures and combinations thereof. As was stated in the preceding, the contents of the container are preferably kept under a pressure greater than atmospheric pressure in order to achieve rapid evaporation of the propellant gas upon application of the cooling medium to the skin.

The present invention further provides a spacer that can be connected to the nebulizer as described above. Specifically it has been found that, for example, if a cooling medium is used to cool the skin to be treated, the temperature to be reached depends on the distance between the nozzle of the nebulizer and the surface to be treated. Therefore the invention provides a spacer which is designed for adjustment of the distance between the nozzle of the nebulizer and the surface to be treated. By positioning the nozzle at a greater distance from the surface to be treated, a lower temperature can be achieved than if the surface to be treated is located at a shorter distance from the nozzle. For this purpose the spacer preferably comprises a displacing element for adjustment of the distance between the surface to be treated and the nozzle, i.e., varying the length of the spacer in the lengthwise direction.

The present invention also provides a spacer that can be connected to the nebulizer described above, wherein the spacer is connected to a cover means provided with an opening and wherein the center axis of the stream or spray to be generated by the nebulizer extends through the opening. The spacer is also designed for fixing the minimal distance between the nozzle attached to the nebulizer and the opening provided in the cover means, wherein the size of the opening provided in the cover means is variable.

The spacer of the present invention has the advantage that as a result of the ability to vary the size of the opening provided in the cover means, the liquid to be applied to a surface, such as a cooling medium, and/or the solid, such as a coating, can be regulated. In consequence it is possible by means of the spacer of the present invention to accurately determine the surface to be treated. In this way it is possible to prevent the surrounding surface, which is not to be treated, from coming into contact with the liquid and/or solid material. In particular, when a cooling medium such as that described above is used, wherein temperatures below the freezing point are achieved, it is desirable to prevent contact of the surrounding skin with the cooling medium in order to enhance comfort for the user.

In one embodiment the valve and/or the nozzle of the nebulizer that can be connected to the spacer can be coupled with an actuating element, which actuating element is integrated in the spacer. In one embodiment variant the spacer comprises an actuating element that extends outside of the spacer. Such an actuating element can, for example, be made in the form of a control button or lever. The actuation of a stream or spray can be accomplished by pressing the control button or moving the lever. To permit easy operation of the spacer and the nebulizer that can be coupled to it, the actuating element is preferably integrated in the spacer. In such a variant embodiment wherein the actuating element is integrated in the spacer, it is possible to actuate the generation of a stream or medium by pressing the container of the nebulizer toward the spacer. The application of a stream or spray, for example a cooling medium, to the skin in such a manner prevents the initial position of the spacer set by the user and the opening located in the cover means relative to the surface to be treated, such as the skin, from being changed unintentionally at the time of actuation of the nebulizer. In addition, upon removal of the nebulizer, whether deliberately or unintentionally, the inlet of the stream or spray will be blocked. Such an integration of the actuating element in the spacer therefore prevents the unintentional application of a liquid, such as a cooling medium, or a solid substance, such as a coating, to surrounding surfaces such as the skin or sensitive organs such as the eye of the user, to the benefit of safety for the user and the accuracy of the process.

As was already mentioned above, the spacer of the present invention is designed for fixing the minimal distance between the nozzle of the container and the surface to be treated or the opening provided in the cover means. In one embodiment the distance between the nozzle of the container and the surface to be treated or the opening provided in the cover means is approximately 0.5 cm to approximately 8.0 cm. It should be noted that to be able to optimally apply a cooling medium to the skin of a person or animal, the distance is preferably approximately 0.5 cm to approximately 7.0 cm, approximately 1.0 cm to approximately 4.0, approximately 1.5 cm to approximately 3.0 cm or approximately 2.0 cm.

The spacer of the present invention may take various shapes. Preferably the shape of the spacer provides that the stream or spray to be generated will have clear access to the opening formed in the cover means connected with the spacer. The shape of the spacer can therefore be selected from a cylinder, truncated cone, hyperboloid of one sheet, elliptical paraboloid and variants thereof. The spacer can have a completely closed shape, which prevents the user from accidentally touching the stream or spray for example with the fingers during the application of the stream or spray onto a surface to be treated. However, the spacer can also be provided with openings or a very open shape to facilitate actuation of the valve by the user and/or to promote evaporation of for example the propellant gas or cooling medium or to observe the stream more clearly.

Like the spacer, the cover means connected to the spacer can assume various shapes. Preferably the size of the cover means is greater than the maximal bore size that the stream or spray can assume upon reaching the opening introduced in the cover means. Preferably the cover means is integrated in the form of the spacer.

In one variant embodiment according to the present invention the cover means comprises at least two screen parts movable relative to one another into at least two different positions. Such screen parts are provided for enclosing openings with different dimensions when the screen parts are brought into different positions. The screen parts of the present invention can have different shapes. In one variant embodiment the screen parts overlap one another in all positions. Preferably the screen parts form a diaphragm. A diaphragm of this type provides the possibility for the user to accurately establish the area to be treated.

In one variant embodiment the cover means comprises at least one screen element adjustable strip provided with openings of different dimensions. Preferably the adjustable strip can be moved by guide means belonging to the cover means and/or spacer. Such a screen element in the form of an adjustable strip provides the possibility to create openings with different (predetermined) shapes. In addition, the use of an adjustable strip with openings of different dimensions decreases the likelihood of jamming of the different screen parts as a result of repeated use of the device. Preferably the adjustable strip comprises an adjusting knob for manually moving the adjustable strip.

The opening provided in the cover means according to the present invention, which is bisected by the center axis of the stream, is preferably larger than the largest opening provided in the adjustable strip.

In addition it is possible to arrange the adjustable strip in such a manner that in at least one position the adjustable strip is not provided with an opening through which it is possible to close the opening provided in the cover means. Such a position of the adjustable strip therefore prevents unintentional contact with the stream or spray to be generated by the nebulizer if the nebulizer is accidentally activated.

In an embodiment wherein the actuating element is integrated in the spacer, the spacer is preferably connected to the blocking element, such as a delimiting ring which is placed around the container and provided with a groove extending radially around the center axis, in which the spacer can be rotated radially around the center axis of the nebulizer. Axial movement of the spacer is blocked by the delimiting ring, thus preventing unintentional actuation of the nebulizer. In at least one position the blocking element is provided with an unlocking part, such as a groove extending in the axial direction connected with the groove extending in the radial direction, which makes possible axial movement of the spacer and actuation of the device.

The invention also relates to an assembly comprising the above described nebulizer and the above described spacer, wherein the nebulizer is connected to the spacer. Preferably the container of the nebulizer is provided with a cooling agent for the treatment of a wart located on the skin of a person or animal wherein the opening provided in the cover means is sized so as to only expose the wart. The treatment wherein the opening of the device is sized so as to only expose the wart provides the possibility of only treating the wart without the surrounding skin simultaneously coming into contact with the cooling medium, which increases the comfort for the user.

The present invention further provides a method for the topical cooling of the skin of a person or animal, with the aid of the spacer according to the present invention which can be connected to the nebulizer according to the present invention, comprising the following steps:
  a) placing the cover means on the skin with an opening in the cover means at the skin site to be cooled; and
  b) delivering the cooling medium to the skin by actuating the valve.

In an embodiment of the method according to the present invention, after placing the cover means of the spacer on the skin, the one opening is brought into overlap with the center axis of the nebulizer, wherein the size of the opening corresponds to the size of the area to be cooled.

During step b) the cooling medium can also be supplied in predetermined quantities. However, it is preferred for the cooling medium to be delivered without interruption in step b). Through the uninterrupted, continuous delivery of the cooling medium a lower temperature can be achieved than is usual at this time. Limited cooling of the skin is achieved with a metered dose, such as a predetermined quantity. This limited cooling generally achieves a temperature of down to −20° C. By uninterrupted delivery of the cooling medium a temperature of below −20° C. can be achieved. Preferably the temperature achieved is below −30° C. Through the uninterrupted delivery of cooling medium a temperature can be achieved which corresponds to the boiling point of the propellant gas, or even a temperature below the boiling point of the propellant gas.

In an embodiment of the method according to the present invention the delivery of the cooling medium is released during pressing of the valve and/or nozzle of the nebulizer.

The present invention furthermore provides a cooling medium for use in a nebulizer and/or the assembly according to the present invention, comprising a colloidal mixture comprising a liquid and/or solid material and a propellant gas and at least one active compound. Preferably the active compound comprises a substance that has antiviral activity. The cooling medium according to the present invention has the advantage that in addition to the remediating and/or alleviating effect from cooling the skin of the user by the propellant gas, the skin is also treated with an active compound that has a supplemental remediating effect. Thus an assembly of this type provides the possibility of allowing specific treatment for specific skin conditions. In an embodiment of the present invention the cooling medium comprises an active compound comprising an antiviral agent, terpene and/or essential oil.

As was stated previously, the antiviral agent can preferably comprise replication inhibitors such as cidofovir, acyclovir, pencyclovir and the like. However, other antiviral agents are also conceivable. If an active compound consisting of terpene and/or essential oils is used, they are preferably selected from camphor, menthol, thymol, thyme oil, eucalyptus, eucalyptus citriodora, turpentine, pine oil, Melaleuca alternifolia, menthone, menthyl salicylate, musk oil, bixa orellana, borneol, curcuma oil, peppermint oil, clove oil, fennel oil, basil oil, patchouli oil, alpha-pinene, terpineol, oregano oil, carvacrol and combinations thereof.

As was previously stated, the cooling medium may comprise a propellant gas which comprises a mixture of hydrocarbons. In one embodiment the propellant gas comprises a cooling agent, in particular, a cooling agent with a boiling point below −10° C. Examples of such suitable cooling agents comprise propane, n-butane, 1,1,1,2-tetrafluoroethane, dimethyl ether, dimethyl ether/propane mixture and combinations thereof. As was stated in the preceding, the contents of the container are preferably kept under a pressure greater than atmospheric pressure in order to achieve rapid evaporation of the propellant gas during the application of the cooling medium to the skin.

The present invention also provides a cooling medium for the treatment of a wart on the skin of a person or animal.

The nebulizer according to the present invention can be used for various applications. In order to further clarify the use of the nebulizer according to the present invention, some specific application information will be presented here. It should be noted that the following list of applications is nonlimiting. Specifically, the nebulizer may be used for the application of a colorant, such as a pigment or dye, a lubricating agent, or an adhesive, such as glue, to a surface. The nebulizer can also be used for the application of cosmetics, such as eye shadow or foundation, or a therapeutically active substance to a body surface such as the skin. In addition the nebulizer according to the present invention can be used for the application of a cleaning agent to a surface to be cleaned or the application of a filler into a cavity to be filled.

The nebulizer according to the present invention is more preferably used for the treatment of skin conditions, such as pigmented spots or moles, and/or the disinfection of wounds.

Figure 1:
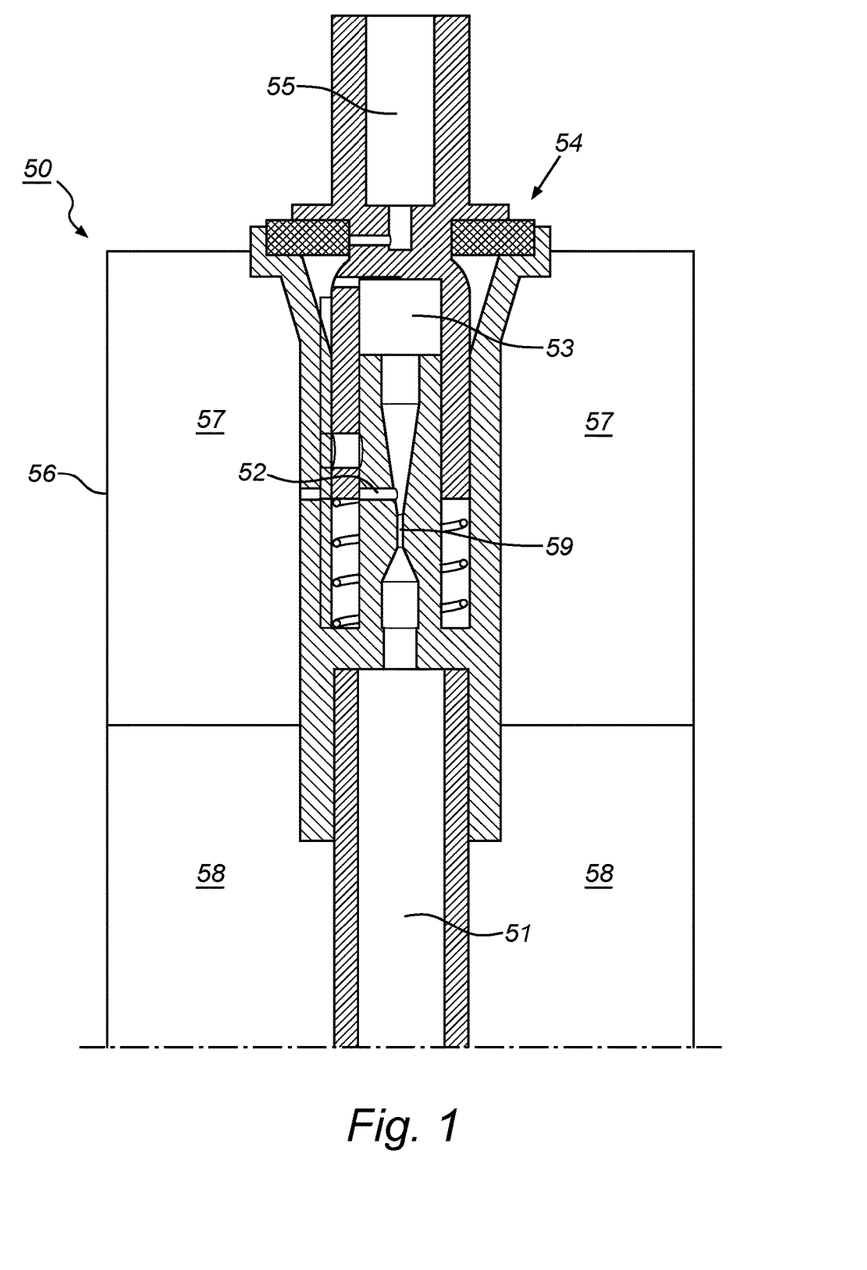
Figure 2:
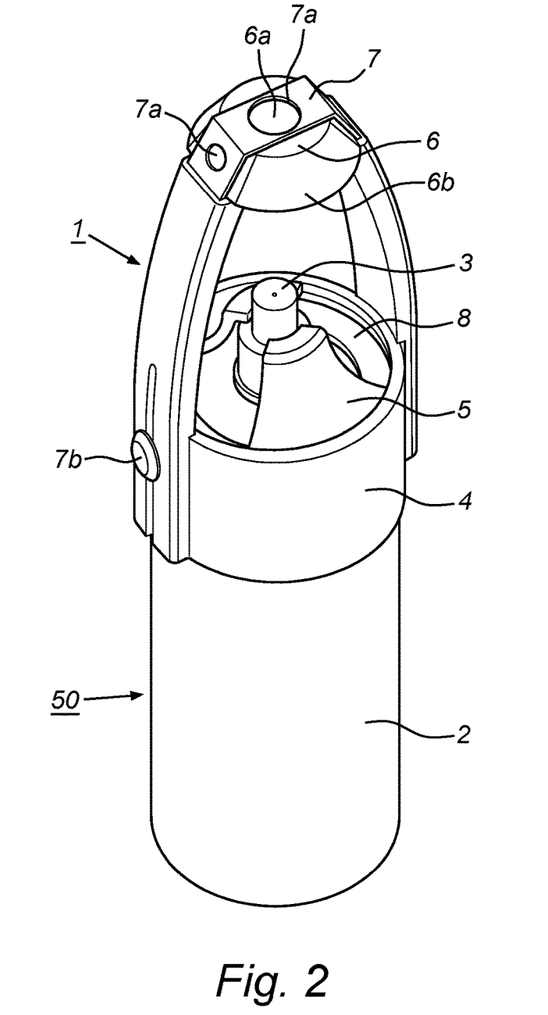
Figure 3:
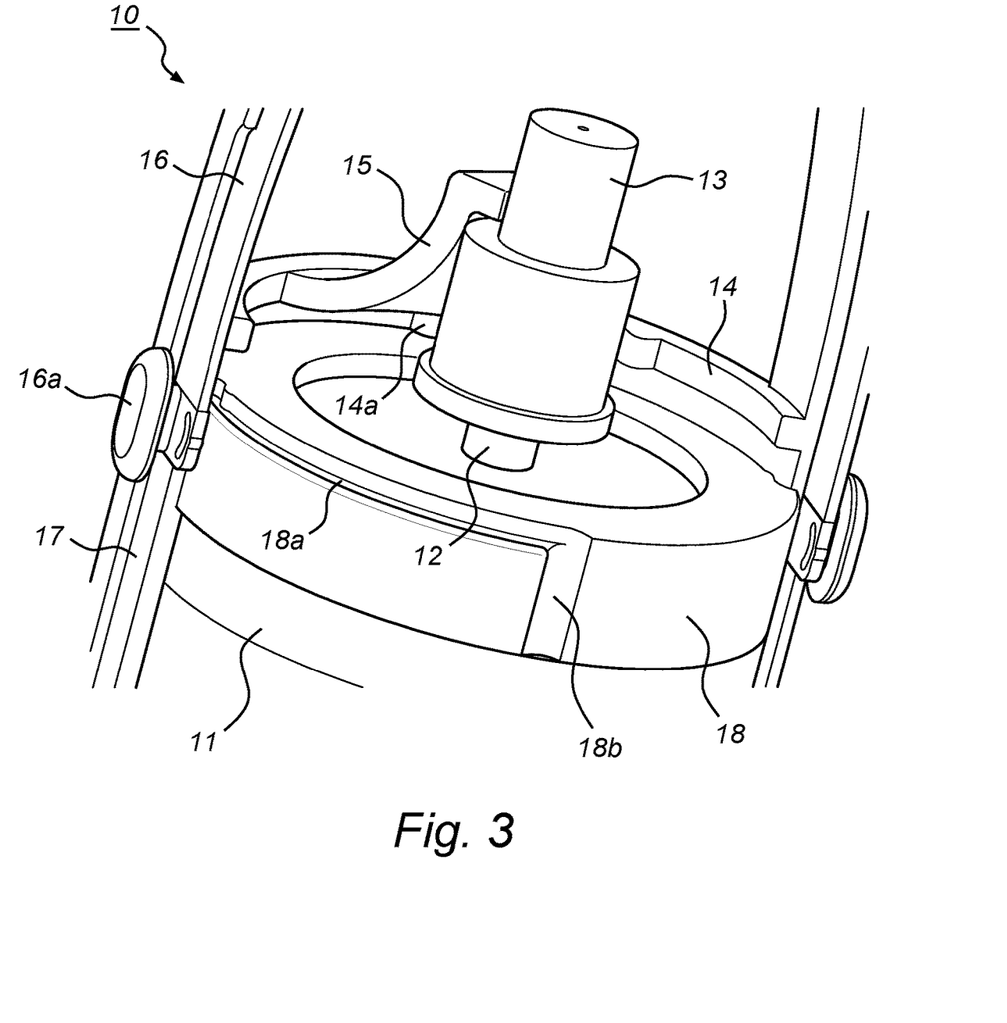
Figure 4:
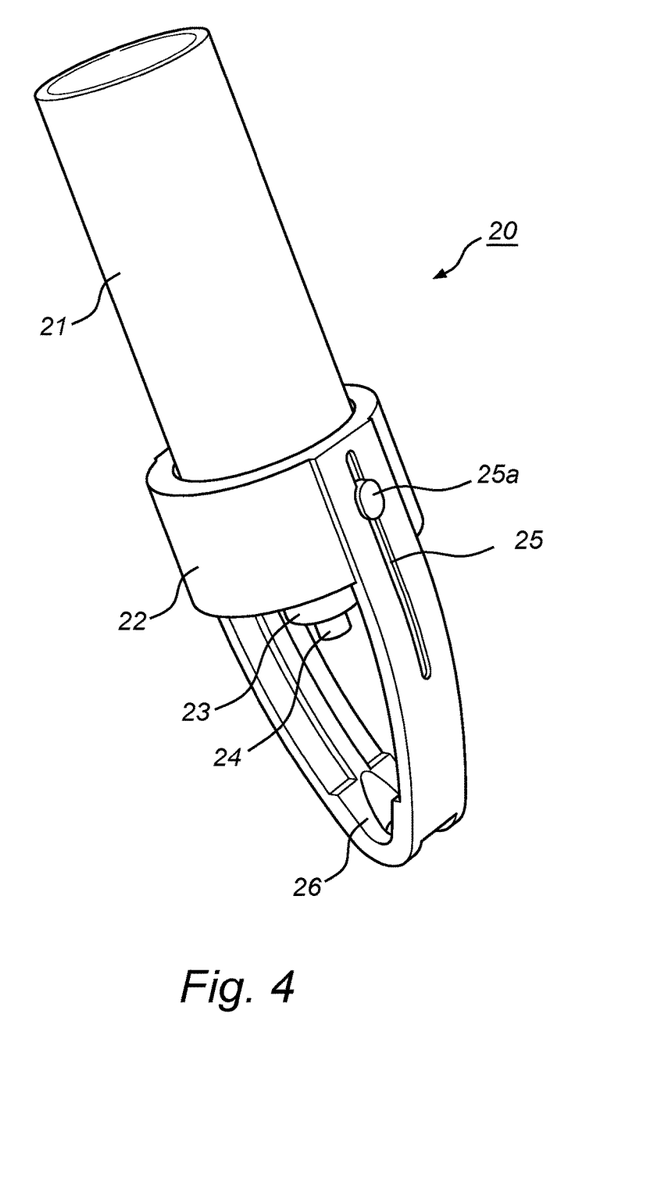
Figure 5A:
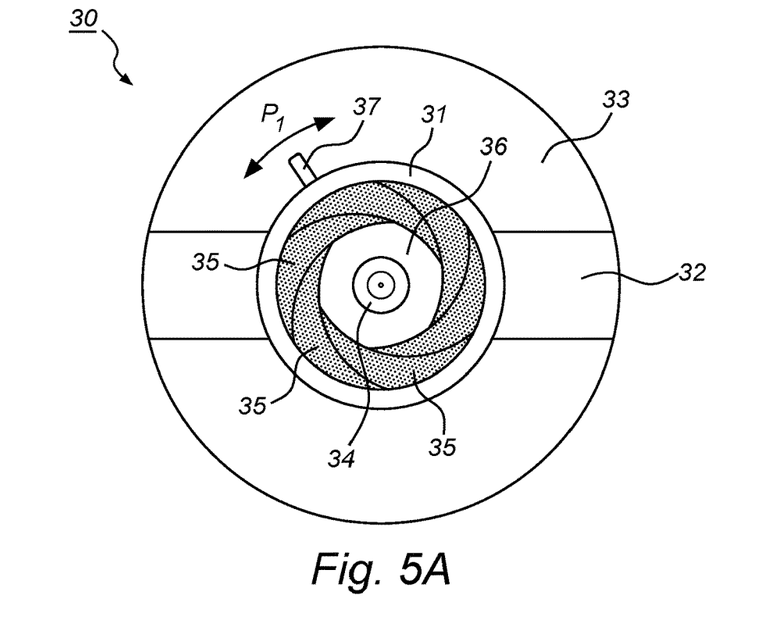
Figure 5B:
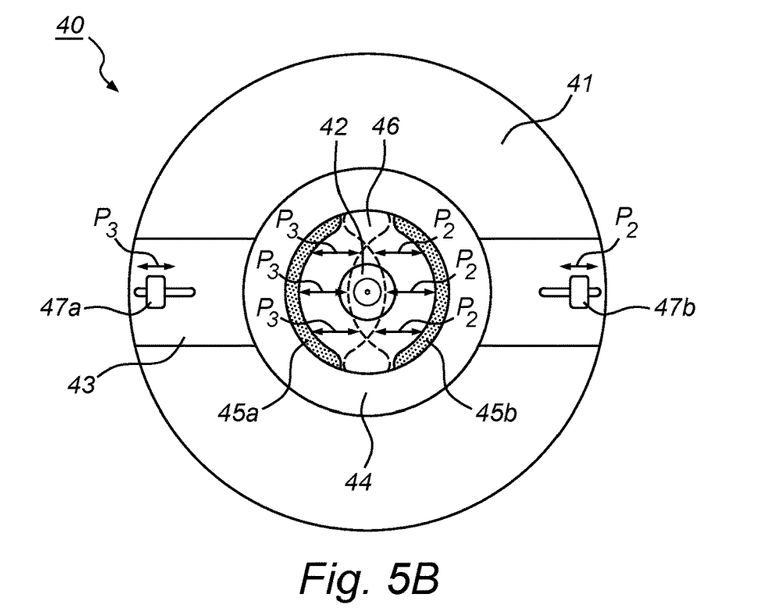

In the following, the present invention will be explained further based on the accompanying drawings, which show the following:

FIG. 1: a schematic representation of the nebulizer according to the present invention;

FIG. 2: a perspective view of an embodiment of the assembly according to the present invention;

FIG. 3: a perspective view of a detail of an embodiment of part of the assembly according to the present invention;

FIG. 4: a perspective view of a embodiment of the assembly according to the present invention;

FIGS. 5*a*-*b*: a rendering of a top view of an embodiment of the assembly according to the present invention;

FIG. 6: a perspective view of a spacer of adjustable length; and

FIG. 7: a schematic representation of the nebulizer according to the present invention with a controllable liquid inlet.

FIG. 1 shows an embodiment of the nebulizer 50 according to the present invention. The nebulizer 50 comprises a first inlet 51, shown here in the form of a tube, and a second inlet 52. Both inlets 51, 52 are connected to a mixing chamber 53 which is incorporated in the valve 54. The valve 54 also comprises a nozzle 55 which is connected to the mixing chamber 53. The container 56 in which the valve 54 is placed comprises a propellant gas 57 (continuous phase) with a liquid 58 (dispersed phase). It is to be noted that the valve also comprises a Venturi 59 which is designed for drawing up liquid 58 when the valve is opened. The assembly as illustrated in FIG. 1 is most efficient in use when the nebulizer 50 is established with the nozzle 55 pointed downward (i.e., at least a position in which the nozzle 55 is at a lower level than the container 56 connected to the valve 54). In such use, upon activating the nebulizer, propellant gas 57 is delivered via the first inlet 51 to which the liquid is to be drawn up by the Venturi effect via second inlet 52. Since the mixing chamber 53 is located inside of the container 56, it should be noted that the pressure in the mixing chamber 53 should be largely equal to the pressure exerted on the liquid 58 and propellant gas 57 located in the container 56.

FIG. 2 shows an embodiment of the assembly 1 according to the present invention in which the spacer 4 is connected to a nebulizer 50 having a container 2. The container 2 as illustrated in FIG. 2 refers to a container for a spray can, and is therefore usually cylindrical in shape. However, any arbitrary shape can be used. The container 2 preferably contains a cooling medium in the form of a liquid which is held under pressure. The nebulizer 50 also comprises a nozzle 3 connected by means of a valve (not shown here) to the container, which upon actuation of the nebulizer 50 produces a directed stream of cooling medium. The assembly 1 also comprises a spacer 4 which in FIG. 2 has a very open elliptical paraboloid shape. In addition the spacer has an integrated actuating element 5 which is connected to the tip 3. The actuating element 5 triggers the generation of a stream of cooling medium by pressing in the tip 3 (and the valve, not shown). In FIG. 2 the actuating element 5 is integrated in the spacer 4, which has the result that a stream of cooling medium can be generated either by pressing in the container 2 or by pressing in the spacer 4. The spacer 4 is connected to a cover means 6. The cover means 6 can assume the form of a cap, wherein the cover means also comprises an opening 6*a* (the outline of which is not visible in FIG. 2). Preferably the cover means 6 comprises an edge 6*b* directed toward the outside, which obstructs the application of cooling medium on the surrounding skin. The spacer 4 also comprises an adjustable strip 7 which is provided with openings 7*a* of different dimensions. FIG. 2 illustrates two such openings 7*a*. The adjustable strip 7 can be adjusted by the user by moving the adjusting knob 7*b*. The spacer 4 is provided with guides (not illustrated), which guide the adjustable strip 7 during the moving of the adjustable strip 7 and the positioning of the desired opening 7*a* in front of the opening 6*a* of the cover means 6. The assembly 1 of FIG. 2 also comprises a delimiting ring 8 for blocking the spacer 4 in at least one position.

FIG. 3 shows a detailed rendering of part of an embodiment of the assembly 10 according to the present invention. In FIG. 3 the nozzle 13 is connected to a valve 12 which is connected to the container 11, which container contains a cooling medium (not illustrated here). FIG. 3 also shows a part of the spacer 14 which comprises an integrated actuating element 15. In addition, the assembly 10 of FIG. 3 comprises an adjustable strip 16 which has an adjusting knob 16*a*. The openings of different dimensions made in the adjustable strip 16 are not shown in FIG. 3. The adjustable strip 16 can be moved by guiding in the guides 17 placed in the spacer 14. The assembly 10 also comprises a delimiting ring 18 which comprises a groove 18*a* which limits the movement of the spacer 14 to that of making a radial rotating movement. The delimiting ring 18 is also provided with a groove 18*b* extending in the axial direction which enables pressing the spacer 14 into a predetermined position and thus actuation of the assembly 10.

FIG. 4 shows an embodiment of the assembly 20 according to the present invention comprising a container 21 and a spacer 22. Also shown in FIG. 4 is the actuating element 23 which is connected to the nozzle 24. The assembly 20 also shows an adjustable strip 25 having an adjusting knob 25*a* for moving the adjustable strip 25. The cover means 26 is integrated in the spacer 22.

FIG. 5*a* illustrates an embodiment of the assembly 30 comprising a spacer 32 connected to a container 33. The spacer comprises a cover means 31. The container 33 also comprises a nozzle 34 connected to a valve (not visible here). The cover means 31 comprises screen parts 35 that overlap one another in all positions. The screen parts 35 as illustrated in FIG. 5*a* together form a diaphragm which describes an opening 36 variable in size. The user can vary the size of opening 36 by moving lever 37 in one of the directions indicated by arrow $P_1$.

FIG. 5*b* illustrates an embodiment of the assembly 40 comprising a container 41 and a nozzle 42 attached to a valve (not visible here). The container 41 is connected to a spacer 43. The spacer 43 is connected to a cover means 44 comprising screen parts 45*a*, 45*b*. The screen parts 45*a*, 45*b* in this embodiment are formed by adjustable strips which are separate from one another and which can overlap one another in the opening 46 made in the cover means. The ends of the adjustable strips 45*a*, 45*b* preferably describe a V-shape (not illustrated here) or half circle. In FIG. 5*b* the ends of the adjustable strips 45*a*, 45*b* are located some distance apart, but preferably the ends of the adjustable strips 45*a*, 45*b* overlap to prevent the ends of the adjustable strips 45*a*, 45*b* from abutting against one another when they are moved together and thus blocking further movement of the adjustable strips 45*a*, 45*b*. However, the ends of the adjustable strips 45*a*, 45*b* can be shaped such that the adjustable strips 45*a*, 45*b* overlap when they are being moved toward one another but without coming to rest against one another. The spacer 43 comprises at least two adjusting knobs 47a, 47b for manually moving the adjustable strips 45a, 45b. A first adjustable strip 45a can be moved by means of a first adjusting knob 47a by moving the adjusting knob 47a in one of the directions indicated by arrow $P_3$. As a result of the movement of the adjusting knob 47a, the end of adjustable strip 45a will also move in a direction indicated by arrows $P_3$. A second adjustable strip 45b, independently of the first adjustable strip 45a, can be moved by means of a second adjusting knob 47b by moving adjusting knob 47b in one of the directions indicated by arrow $P_2$. As a result of the movement of the adjusting knob 47b the end of adjustable strip 45b will also move in a direction indicated by arrows $P_2$. The size and shape of opening 46 can be varied by moving one or both ends of adjustable strips 45a, 45b.

Figure 6:
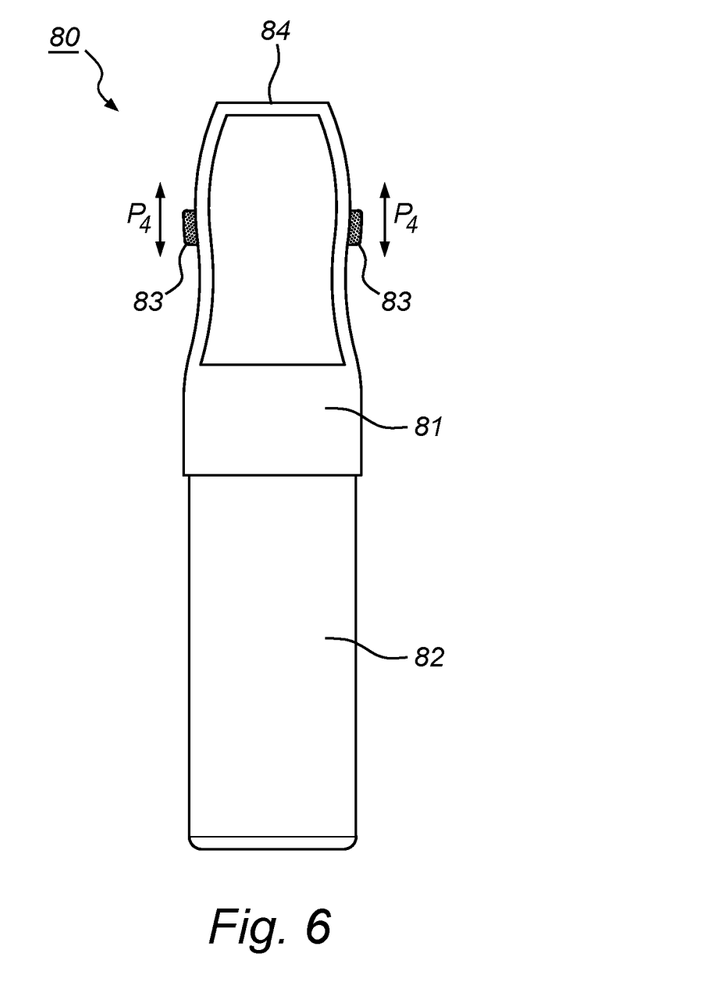

FIG. 6 illustrates an embodiment of the assembly 80 comprising a spacer 81 which is connected to a nebulizer 82. The spacer 81 is provided with adjusting knobs 83 for adjustment of the distance between the nozzle (not illustrated here) and the opening 84 provided in the spacer 81 or the surface to be treated (not illustrated here) in the direction of arrows $P_4$.

Figure 7:
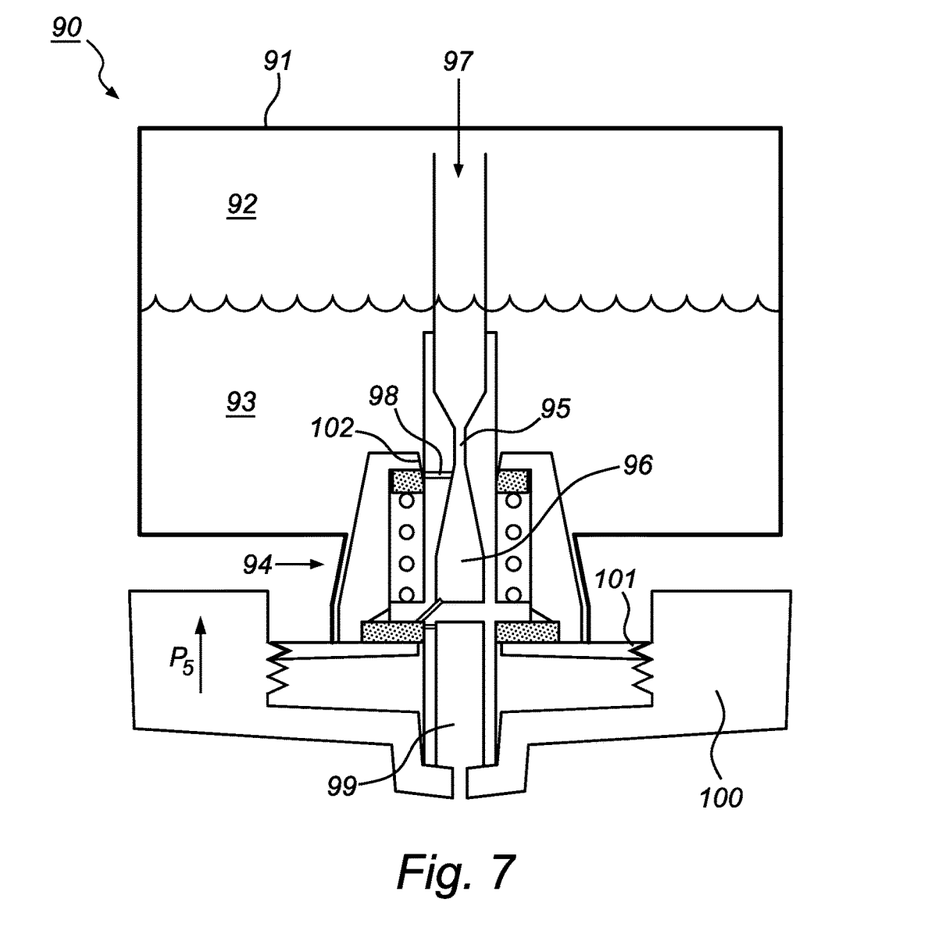

FIG. 7 illustrates an embodiment of a nebulizer 90 comprising a container 91 comprising a propellant gas 92 and a liquid 93. The nebulizer 90 also comprises a valve 94 in which a Venturi 95 is affixed which connects with a mixing chamber 96. The valve 94 comprises a first inlet 97 for delivering the propellant gas 92 and a second inlet 98 for delivering the liquid. The valve 94 also comprises a nozzle 99 which is coupled with an actuator 100. The actuator 100 is connected by means of a screw connection 101 to the nozzle 99. Screwing the actuator 100 farther onto the nozzle 99, i.e., in the direction of arrow $P_5$ means that the nozzle 100 and the valve 94 cannot be pressed in as far. As a result, the second inlet 98 will also be moved over a short distance. As is apparent from the assembly shown, in this way the opening of the second inlet 98 is decreased. The sloping walls 102 affixed in the valve ultimately determine the final bore of the second inlet 98 and therefore the quantity of liquid 93 that is drawn in through the valve 94. Naturally, screwing the actuator 100 farther out in a direction opposite to the direction of arrow $P_5$ will result in a larger quantity of liquid 93 being able to be drawn up. Then the opening of the second inlet 98 will ultimately come to be completely free with regard to the sloping wall 102 affixed in the valve 94.

The invention claimed is:

1. Nebulizer device (1, 10, 20, 30, 40, 50, 80, 90) for the topical application of a liquid to a surface, comprising:
 a container (2, 11, 21, 33, 41, 56, 91) comprising a propellant gas (57, 92) and a liquid (58, 93);
 an actuatable valve (12, 54, 94) attached to the container (2, 11, 21, 33, 41, 56, 91); and
 a nozzle (3, 13, 24, 34, 42, 55, 99) attached to the valve (12, 54, 94), designed for generating a stream or spray,
 wherein the valve (12, 54, 94):
  comprises a mixing chamber (53, 96) attached to the nozzle (3, 13, 24, 34, 42, 55, 99); and
  comprises a first (51, 97) and a second (52, 98) inlet attached to the mixing chamber (53, 96),
 wherein the mixing chamber (53, 96) is provided with a Venturi (59, 95) and is designed for forming a colloidal mixture before delivering the colloidal mixture to the nozzle (3, 13, 24, 34, 42, 55, 99),
 characterized in that the device (1, 10, 20, 30, 40, 50, 80, 90) is configured such that in use:
  the first (51, 97) inlet delivers the propellant gas (57, 92) to the mixing chamber (53, 96) and the second (52, 98) inlet delivers the liquid (58, 93) to the mixing chamber (53, 96); and
  the first inlet (51, 97) connects to the Venturi (59, 95) such that the liquid (58, 96) is delivered via the second inlet (52, 98) by using the suction effect of the Venturi (59, 95); and
  the colloidal mixture formed in the mixing chamber (53, 96) comprises a dispersed phase consisting of the liquid (58, 96) and a continuous phase consisting of the propellant gas (57, 92).

2. Device (1, 10, 20, 30, 40, 50, 80, 90) as claimed in claim 1, characterized in that the liquid (58, 93) is selected from the group consisting of liquid nitrogen, dimethyl ether, propane and dimethyl ether/propane mixture.

3. Device (1, 10, 20, 30, 40, 50, 80, 90) as claimed in claim 1, characterized in that the first (51, 97) and/or second (52, 98) inlet is provided with inlet blocking means which closes the first (51, 97) and/or second (52, 98) inlet when the device is in a pre-defined inactive orientation.

4. Device (1, 10, 20, 30, 40, 50, 80, 90) as claimed in claim 1, characterized in that in the closed state the pressure in the container (2, 11, 21, 33, 41, 56, 91) and the pressure in the actuatable valve (12, 54, 94) attached to the container (2, 11, 21, 33, 41, 56, 91) is the same.

5. Device (1, 10, 20, 30, 40, 50, 80, 90) as claimed in claim 4, characterized in that the pressure is greater than 2.0 bar.

6. Device (1, 10, 20, 30, 40, 50, 80, 90) as claimed in claim 1, characterized in that the device (1, 10, 20, 30, 40, 50, 80, 90) further comprises a blocking element for blocking the valve in at least one position.

7. Device (1, 10, 20, 30, 40, 50, 80, 90) as claimed in claim 1, characterized in that the propellant gas (57, 92) comprises a cooling agent with a boiling point below $-10°$ C.

8. Device (1, 10, 20, 30, 40, 50, 80, 90) as claimed in claim 7, characterized in that the cooling agent is selected from the group consisting of propane, n-butane, 1,1,1,2-tetrafluoroethane, dimethyl ether and dimethyl ether/propane mixture.

9. Device (1, 10, 20, 30, 40, 50, 80, 90) as claimed in claim 1, wherein the device (1, 10, 20, 30, 40, 50, 80, 90) is connected to a spacer (4, 14, 22, 32, 43, 81), which spacer (4, 14, 22, 32, 43, 81) is designed for adjustment of the distance between the nozzle (3, 13, 24, 34, 42, 55, 99) of the device (1, 10, 20, 30, 40, 50, 80, 90) and the surface to be treated, said spacer (4, 14, 22, 32, 43, 81):
 is connected to a cover means (6, 26, 31, 44) provided with an opening (6a, 36, 46, 84), wherein the center axis of the stream or spray to be generated by the device (1, 10, 20, 30, 40, 50, 80, 90) extends through the opening (6a, 36, 46, 84); and
 is designed for fixing the minimal distance between the nozzle (3, 13, 24, 34, 42, 55, 99) attached to the device (10, 20, 30, 40, 50 80, 90) and the opening (6a, 36, 46, 84) provided in the cover means (6, 26, 31, 44),
 wherein the size of the opening (6a, 36, 46, 84) provided in the cover means (6, 26, 31, 44) is variable, characterized in that the cover means (6, 26, 31, 44) comprises at least two screen parts (35, 45a, 45b) movable relative to one another into at least two different positions, and that in the different positions openings (6a, 36, 46, 84) with different dimensions are enclosed.

10. Device (1, 10, 20, 30, 40, 50, 80, 90) as claimed in claim 9, characterized in that the cover means (6, 26, 31, 44)

comprises at least one screen element adjustable strip (7, 16, 25) provided with openings (7*a*) of different dimensions, which can be moved by guide means belonging to the cover means (6, 26, 31, 44) and/or the spacer (4, 14, 22, 32, 43, 81).

11. Method for treating the skin of a person or animal using the device (1, 10, 20, 30, 40, 50, 80, 90) as claimed in claim 1, comprising the following steps:
  i. providing the device (1, 10, 20, 30, 40, 50, 80, 90) as claimed in claim 1;
  ii. bringing the device (1, 10, 20, 30, 40, 50, 80, 90) into an active orientation; and
  iii. delivering the liquid to the skin by actuating the valve (12, 54, 94).

12. Method as claimed in claim 11, characterized in that the person or animal is suffering from skin problems or skin conditions.

13. Method as claimed in claim 12, characterized in that the skin problems are selected from the group consisting of topical burns, pustules, itching and skin irritation.

14. Method as claimed in claim 12, characterized in that the skin conditions include warts.

15. Method as claimed in claim 11, characterized in that the method further comprising the step of, in case present, placing the cover means (6, 26, 31, 44) on the skin during step ii)) and bringing the opening (6*a*, 36, 46, 84) into overlap with the center axis, wherein the size of said opening (6*a*, 36, 46, 84) corresponds to the size of the area to be cooled.

16. Method as claimed in claim 11, wherein in step iii) the liquid is delivered without interruption.

\* \* \* \* \*